(12) United States Patent
Moore

(10) Patent No.: US 7,273,449 B2
(45) Date of Patent: Sep. 25, 2007

(54) PHALLOPLASTY

(76) Inventor: Colin Campbell Marshall Moore, 2/238 Falcon Street, North Sydney, New South Wales 2060 (AU)

( * ) Notice: Subject to any disclaimer, the term of this patent is extended or adjusted under 35 U.S.C. 154(b) by 0 days.

(21) Appl. No.: 10/520,959

(22) PCT Filed: Apr. 3, 2003

(86) PCT No.: PCT/AU03/00400

§ 371 (c)(1),
(2), (4) Date: Sep. 15, 2005

(87) PCT Pub. No.: WO03/082120

PCT Pub. Date: Oct. 9, 2003

(65) Prior Publication Data

US 2006/0157066 A1   Jul. 20, 2006

(30) Foreign Application Priority Data

Apr. 3, 2002 (AU) .................................. 31403/02

(51) Int. Cl.
*A61F 5/00* (2006.01)
(52) U.S. Cl. ...................................................... 600/38
(58) Field of Classification Search ............ 600/38–41; 128/897–898
See application file for complete search history.

(56) References Cited

U.S. PATENT DOCUMENTS 5,921,246 A * 7/1999 Cho ............................ 128/898
6,173,714 B1 * 1/2001 Cho ............................ 128/898

FOREIGN PATENT DOCUMENTS

AU           53864/98           8/1889
AU         B- 79900/98          2/1999

OTHER PUBLICATIONS

G. Alter, "Girth Enlargement" (online) (retrieved May 14, 2003), earliest known publication date (via URL:http://wwww.archive.org) is May 5, 1998 Retrieved from the Internet URL:http://www.altermd.com/penhancement/girth.htm.
"Penis Lengthening Surgery—Questions and Answers" (online) (retrieved May 14, 2003), earliest known publication date (via URL:http://www.archive.org) is Jan. 30, 1997 Retrieved from the Internet URL:http://www.psurg.com/PL4QA.htm.
D. James, "The Perfect Penis in about an Hour" (online) (retrieved May 14, 2003), earliest known publication date (via URL:http://www.archive.org) is Mar. 3, 2001; Retrieved from the Internet URL:HTTP:WWW.PSURG.COM/HUMBER99.HTML.
G. J. Alter, "Penile Enlargement Surgery", *Techniques in Urology*, 1998, vol. 4, No. 2, pp. 70-76.
G. J. Alter, "Augmentation Phalloplasty," *Urologic Clinics of North America*, 1995, vol. 22, No. 4, pp. 887-902.
T. F. Lue and A. I. El-Sakka, "Lengthening Shortened Penis Caused by Peyronie's Disease Using Circular Venous Grafting and Daily Stretching with a Vacuum Erection Device," *Journal of Urology*, Apr. 1999, vol. 161, pp. 1141-1144.
E. Austoni, A. Guarneri and A. Cazzaniga, "A New Technique for Augmentation Phalloplasty: Albugineal Surgery with Bilateral Saphenous Graft—Three Years of Experience." *European Urology*, 2002 vol. 42, pp. 245-253.
E. Austoni, A. Guarneri, and G. Gatti, "Penile elongation and thickening—myth? Is there a cosmetic or medical indication?", *Andrologia*, 1999, 31 (Suppl 1) pp. 45-51.
L. Shirong, Z. Xuan, W. Zhengxiang, F. Dongli, W , Julong, and Y Dongyun, "Modified Penis Lengthening Surgery: Review of 52 Cases," *Plastic and Reconstructive Surgery*, Feb. 2000, pp. 596-599.
G. Rigaud and R. E. Berger, "Corrective Procedures for Penile Shortening due to Peyronies's Disease," *The Journal of Urology*, Feb. 1995, vol. 153, pp. 368-370.
International Search Report for International Application No. PCT/AU03/00400, Jul. 7, 2003.

* cited by examiner

*Primary Examiner*—Samuel G Gilbert
(74) *Attorney, Agent, or Firm*—Knobbe, Martens, Olson & Bear, LLP

(57) ABSTRACT

A method of penis lengthening including dividing the suspensory ligament down to the inferior public arch, dividing the fundiform ligaments; or dividing the first and second corpus cavernosum circumferentially. A method of widening a penis where a dermal fat graft is sutured to the exposed Bucks fascia. Post operative drug and exercise to maintain the outcome of penis lengthening or widening.

5 Claims, No Drawings

PHALLOPLASTY

RELATED APPLICATIONS

This application is the U.S. National Phase of PCT/AU03/00400 filed Apr. 3, 2003 and claims priority to Australian Application No. 31403/02 filed Apr. 3, 2002, which are hereby incorporated by reference herein.

This invention relates to enhancement phalloplasty, which is a surgical procedure to modify the human penis, normally by increasing the length of or widening the penis.

BACKGROUND

There are several reasons for persons requiring operations of this type. The first is for persons who are born with small penises. These persons can often believe that they are the subject of derision and ridicule and the lack of size of the appendage can be emotionally very difficult for them.

A second is where persons, either for personal pleasure or for professional reasons, such as strip-tease dancers, actors and the like, wish to be seen to have a large penis.

There have been previously proposed methods of enhancement phalloplasty but these have not been fully successful.

The major object of the invention is to provide methods of enhancement phalloplasty which provide satisfactory results and which are safe procedures and which result in lengthening the penis in both the flaccid and erect states.

The applicant has disclosed basic surgical procedures in earlier filed patent applications including Australian Patent Applications 28601/97, 53864/98 and 79900/98. However these applications are for a base surgical procedure. It is an object of the present invention to combine these surgical procedures and others with post-operative treatment methods thereby to maintain the outcome of the basic surgical procedure.

BRIEF DESCRIPTION OF INVENTION

Accordingly, in one broad form of the invention there is provided a method for penile enlargement further including the step of application of a post-operative treatment regime.

Accordingly, in another broad form of the invention there is provided a method for penile enlargement further including the step of application of a post-operative treatment regime thereby to maintain outcome of enlargement.

Accordingly, in yet another broad form of the invention there is provided a method of widening a penis wherein a dermal fat graft comprising a block of fat and attached dermis is excised from the patient, the penis is degloved, the dermal fat graft is sutured to the exposed Bucks fascia and then reducing the penile skin; said method further including the step of following a post-operative treatment regime.

Preferably the dermal fat grafts are harvested from either the buttocks, lower back or lower abdomen.

Accordingly, in yet another broad form of the invention there is provided a method of lengthening the penis of a male which includes the steps of placing the suspensory ligament under tension in the inferior direction; dividing the suspensory ligament against the body of the symphysis pubis down to the inferior pubic arch and along the inferior surface of both the right and left conjoined inferior pubic rami; effecting suturing to retain the penis released from the suspensory ligament in an inferior position by coapting the proximal medial attachments of the right and left gracilus muscle together ventral the released penis, dividing the fundiform ligaments, drawing the skin of the junction site of the scrotum and the perineum mediosuperiorally so as to attach it to the symphysis pubis thereby pushing the skin adjacent thereto along the newly exposed shaft of the penis and suturing this to retain this position; said method further including the step of following a post operative treatment regime.

Preferably followed by the insertion of additional sutures through the anterior surface of the symphysis pubis; said sutures also placed through the margins of the pubic skin wound and tied in such a manner as to pull suprapubic skin down infrapubically.

Preferably the number of said additional sutures inserted is 1 or more.

Preferably the number of said additional sutures is determined by the width of the symphysis pubis.

Preferably including the step of dividing the fundiform ligament prior to said step of drawing the skin of the junction site of the scrotum.

Accordingly, in yet another broad form of the invention there is provided a method of widening a penis wherein a block of fat and attached dermis (dermal fat graft) is excised from the patient, the penis is degloved, the dermal fat graft is sutured to the exposed Bucks fascia and then reducing the penile skin.

Preferably the dermal fat grafts are harvested from either the buttocks, lower back or lower abdomen.

Preferably the dermal fat graft is sutured to the exposed Bucks fascia prior to the tying of the sutures which maintain the lengthening of the penis.

Accordingly, in yet another broad form of the invention there is provided a method of enhancement phalloplasty of a human penis in patients who are about to have or already have in place an artificial erection device; said penis having a structure including a first corpus cavernosum, a second corpus cavernosum, a corpus spongiosum, a Buck's fascia and a dorsal neurovascular bundle; said method including the steps of degloving the penis to expose the Buck's fascia; freeing the dorsal neurovascular bundle and separating the corpus spongiosum from the inferior surface of both said first and said second corpus cavernosum; dividing said first and second corpus cavernosum circumferentially; said method further including the step of following a post-operative treatment regime.

Preferably said step of separating the corpus spongiosum from the inferior surface of both said first and said second corpus cavernosum comprises a dissection so as to enable the first and second corpus cavernosum to be elongated without dividing the corpus spongiosum.

Preferably said artificial erection device comprises a corporal cylinder which is longer than the corporal cylinder presently in place, either where the patient already has an artificial erection device in place or longer than the corporal cylinder which was measured when the corporotomy and dilatation of the corpus was performed earlier in the procedure.

Preferably the increase in length of the corporal cylinder is of the order of one or more cm.

Preferably a gap formed in the first or second corpus cavernosum is filled by suturing in place an inverted dermal graft from which the epidermis has been removed.

Preferably the dermo epidermal surface is the inner most surface applied to the corporal cavity.

Preferably widening of the penis is also required and wherein widening is effected by using a dermal fat graft.

Preferably the fat graft is sutured to the exposed Bucks fascia and when the graft reaches a defect in the Buck's fascia corresponding to the division of the first or second corpus cavernosum the edges of the graft are sutured to the Buck's fascia circumferentially and to a distal portion of the first or second corpus cavernosum without dividing the graft as a separate phenomenon.

Preferably if the patient has a very thickened wall of the first or second corpus cavernosum, a first dermal fat graft is placed into the defect in the Buck's fascia and then a second dermal fat graft is placed into the defect.

Preferably if the patient has a very thickened wall of the corpus cavernosum, the gap in the wall of the corpus cavernosum is filled by using a gortex graft, a saphenous or other vein patch, temporalis or other fascia such as the fascia lata or dexon mesh or silastic sheeting or other appropriate material and then said second dermal fat graft is applied.

Preferably further including an additional step wherein the degloved penis is reduced and the proximal wounds are trimmed and closed in layers.

Accordingly, in yet another broad form of the invention there is provided a method of enhancement phalloplasty substantially as hereinbefore described with reference to the examples of the particular operations given in the specification.

Preferably penile enlargement comprises one or more of lengthening or widening.

Preferably further including the step of treatment for buried penis condition.

Preferably said post-operative treatment regime comprises application of a drug treatment regime.

Preferably said post-operative treatment regime comprises application of an exercise regime.

Accordingly, in yet a further broad form of the invention there is provided an exercise regime for application following application of the above described method.

Accordingly, in yet a further broad form of the invention there is provided a drug treatment regime for application following application of the above described method.

Accordingly, in yet a further broad form of the invention there is provided a method of lengthening and widening a penis, the lengthening using the method as described above wherein a block of fat and attached dermis (dermal fat graft) is excised from the patient, the penis is degloved, the dermal fat graft is sutured to the exposed Bucks fascia prior to the tying of the sutures which maintain the lengthening of the penis.

DETAILED DESCRIPTION OF PREFERRED EMBODIMENTS

In order that preferred embodiments of the invention may be more readily understood, I will describe certain procedures in greater detail below.

The first of these has to do with penile enlargement. This involves suprapubic (or other type) incision and exposure of the suspensory and fundiform ligaments of the penis and their division under direct vision from the suprapubic area and the inferior bodies of the pubic arch (i.e. all of the antero-inferior surface of the pubic symphysis. The penis is depressed posteriorly by approximating the medial edges of the upper ends of the right and left Gracilis muscle in front of the penis. The suprapubic skin is rearranged (by Zplasty, excision or a combination of both) and sutured together and to the superior and anterior surfaces of the body of the pubis right and left.

To aid in the full understanding of the invention, I will more fully describe the procedures of preferred embodiments:

Penile Lengthening

With the patient under general anesthesia and in the supine position the lower abdomen, perineum and thighs are prepared and draped. In the classic procedure, a transverse suprapubic incision is made measuring approximately 3 cm in length. Various other incision can be used such as W plastys, Z plastys, vertical and peno-scrotal incisions and the like.

The incision site and the adjacent mons tissues are infiltrated with local anesthetic and adrenalin. The tissues overlying the mons veneris are separated laterally and the fundiform and suspensory ligaments of the penis are visualized.

Dissection is carried down by a blunt technique on either side of the suspensory ligament which is then divided under direct vision using diathermy. The dissection is carried out against the body of the symphysis pubis down to the inferior pubic arch level and along the conjoined rami of ischium and pubis for a short distance. During the maneuver the assistant pulls the penis in an inferior direction placing the ligament under tension and it can be seen under direct vision and the neurovascular bundles can also be directly visualized and preserved.

At this point, an O Maxon (or other suture material) deep stay suture is inserted into the deep surface of the pubic symphysis and then carried around the right Gracilis fascia and muscle across to the left Gracilis fascia and muscle and the suture left loose. A second O Maxon (or other suture material) is then inerted distal to the first suture so as to further coapt the right and left Gracilis muscles in front of the penis. Two more deep stay sutures of O Maxom (or other suture material) are then inserted into the pubic bone inferior surface laterally and left untied. A fifth, sixth and seventh O Maxon (or other suture material) suture are placed into the very superior edge and anterior surface of the exposed symphysis pubis and left untied.

The first deep stay suture of O Maxon is then tied commencing with the one involving both Gracili which can be observed to approximate in front of the inferiorly depressed shaft of the penis followed by tying the second O Maxon Gracilis suture. The tissues on each side of the mons veneris at this point are then dissected and the fundiform ligaments which are now clearly outlined as a result of this dissection are also divided under direct vision down to but not including the tissues overlying the spermatic cords on either side. The junction of the perineal and scrotal skin on either side is then identified approximately 3 cm lateral to the midline and one each of the remaining third and fourth O Maxon (or other suture material) sutures is/are inserted into the deep layers of the dermis of the scrotum on each side and the sutures tied. This draws the skin of the junction side of the scrotum and perineum mediosuperiorly pushing the skin adjacent to it along the newly exposed shaft of the penis. The fifth, sixth and seventh O Maxon suture are inserted into the deep layers of the suprapubic incision in the centre and on either side and are tied so as to gently curve the skin of the mons veneris down over the top of the symphysis pubis further aiding the movement of the abdominal skin onto the new penile shaft.

After trimming the wound is closed in layers and dressings are applied.

Penile Widening By Dermal Graft

With the patient under satisfactory general anesthesia and in the prone position, the buttock, anal area and thighs are prepared and draped. The areas of incision at the buttock/thigh fold on both legs, which were previously marked, are infiltrated with a mixture of local anesthetic and adrenalin and then the outer layers of the epidermis are dissected off over an area measuring of the order of b 5×10 cm or more cms. The actual size will be determined by the initial size of the penis measured preoperatively. Once the epidermis has been dissected free it is discarded. The exposed dermis, together with its layer of subtenant fat measuring approximately 2 cm deep is excised en bloc using a mixture of cautery and sharp dissection.

The graft is then wrapped in a pack soaked in cold Ringer's solution and kept at room temperature (0 to 10 degrees Centigrade). The wound is closed in layers. Dressings are applied.

The patient is then turned from the prone to the supine position while still anesthetized and the lower abdomen, perineum and thighs prepared and draped.

The area of the incision is then infiltrated with a mixture of local anesthetic and adrenalin.

If widening is done in conjunction with lengthening, the incision is usually transverse though it may be any combination of the incisions described under lengthening, above including the peno-scrotal incision. If widening is done alone then a transverse suprapubic incision is usually used although any of the above incisions may be used.

If the patient is already circumcised, infiltration of the old circumcision scar in its anterior half may also be carried out. If the patient is not circumcised it is necessary to proceed to circumcision usually, as this is a requirement for dermal fat grafting usually (though not always), then the entire circumference of the penis at the proposed circumcision site is infiltrated with local anesthetic and adrenalin.

If the peno-scrotal approach is being used with degloving of the penis, then a completely circumferential infiltrate with local anesthetic is used whether the patient is circumcised or not.

Once the incision, be it peno-scrotal, or more commonly transverse suprapubic, has been carried down to the deeper layers by blunt dissection, the skin and superficial fascia of the penis is separated from the shaft of the underlying penis in its entire length and circumference.

At this point, the anterior half of the old circumcision scar may be reopened (in the case of the suprapubic transverse incision) or the entire old circumcision scar or a new circumcision site is opened in the case of the uncircumcised who require circumcision, and in the case of the peno-scrotal approach in the former. The penis is then degloved. The dermal fat graft is then sutured to the exposed Bucks fascia commencing on the coronal groove distally and going as far proximally as is possible with the wound exposure. This should be at least well down into the infra pubic region of the symphysial or mid-portion of the penile shaft. The graft is attached all around the shaft of the penis leaving only the corpus spongiosum exposed.

The penile skin is then reduced, the circumcision wound (if applicable) is then closed as is the peno-scrotal incision if it has been used after the dartos fascia has been closed.

If the suprapubic incision has been used it is closed in layers. Telfa is applied to the wounds and the penis is encased in a crepe bandage as a moderately compressed dressing.

Combined Penile Lengthening and Widening

With the patient in the prone position, the dermal fat grafts are harvested as described above. The patient is then turned to the supine position and the operation proceeds as described under penile lengthening to the point where all of the deep stay sutures are in place but not tied. At this time, the distal circumferential incision (circumcision site incision if required) is performed, the penile skin is developed and the penis degloved. The dermal fat graft is then sutured into place as described above.

Once the penile skin has been reduced, the deep stay sutures are then tied as described above in regard to penile lengthening and attached to their other structures. All wounds are then closed as described above.

Post-Operative Treatment Regimes

The abovementioned procedures advantageously are applied in combination with one or more of the following post-operative treatment regimes, namely either one or both of the stretching exercise or the drug treatment regime.

Post-Operative Penile Scar Stretching Exercise

THE EXERCISE: The Patient stands with the right leg flexed to 90 degrees at the right (left) hip joint.

The Right (left) foot is resting on a chair or stool such that the right (left) knee is also at a right angle. The right (left) hand is passed around the right (left) thigh from outside, under, & inside the right (left) thigh & using the index finger & thumb of the right (left) hand the Glans (head) of the Penis is grasped (only the Glans & NO part of the shaft skin) & pulled down & back so that the penis is pulled down & back between the Testicles & back towards the Anus. The patient pulls as hard as he can tolerate & should feel a strong pulling sensation at the base of the penis.

TIMING: The exercise consists of ten (10) pulls (five (5) using the right hand & leg , & five (5) using the left hand & leg. Each pull is for ten (10) seconds & the patient may time this using a clock or simply count 1 &, 2 &, 3 &, 4 &, 5 &, 6 &, 7 &, 8 &, 9 &, 10 &. The patient rests for one (1) second reapplies his grip to the Glans & pulls again for another ten (10) seconds.

This is repeated for ten (10) pulls each for ten (10) seconds. Ten (10) such pulls, each for ten (10) seconds constitute one block of exercises. The patient is required to perform three blocks per day viz. one block on first getting out of bed in the morning, one block when he gets home from work, & one block just prior to going to bed at night (a total of thirty (30) pulls per day in three blocks of ten pulls).

It is to be understood that one can use a variety of combinations of timing and number of pulls. Each pull will always be for 10 seconds, or multiples of 10 seconds. The number of pulls may vary and may be in excess of 100. The preferred number of exercise blocks per day is normally 3, but this may be varied to suit the specific situation.

Preferred ranges: 10 seconds minimum with an absolute minimum of 5 seconds. Multiples of this period may run up to a maximum of 100 seconds.

A possible formula to use to determine the overall regime is: pulls×seconds×repetition regime (minimum 300, maximum 1200) which can be termed the penile scar ergonomic factor.

The above regime can be used following one or more of the following operative procedures:

Post Operative Drug Treatment Regime

A treatment regime which can be used to advantage in respect of any of the above described procedures.

Initially, post-operatively a drug treatment regime can include the following:

Cephalexin (Monohydrate)—500 mg orally three times a day for 14 days—controls gram posotro organisms, particularly staff and the like;

Combination: Amoxycillin (Trihydrate) and Clavulamic Acid e.g. Augmentin Duoforte—one tablet twice a day orally for two weeks—deals with organisms not commonly found at the operation site so as to lower wound infection rate;

Al Prazolam—0.5-1 mg orally three times a day for two weeks to suppress erections;

Ketoconazole—400 mg post-operatively three times per day for two weeks—again to suppress erections;

Mersyndol Forte—2 capsules at night for two weeks—again to suppress erection;

Prednisone—A regime of 10 mg three times a day for five days followed by 10 mg twice a day for three days followed by 5 mg twice a day for two days followed by 5 mg once a day for two days—for the purpose of minimising the amount of local tissue swelling.

Treatment of Buried Penis

Now follows a description of the treatment of buried penis by a combination of reconstruction of the pubic area, with elevation of the parapenile and supra-penile tissues so as to reveal the buried penis in conjunction with enhancement phalloplasty as described above.

The purpose of the procedure is to enlarge the penis by recognising that in some individuals in addition to the penis having a small length and diameter it may also be partly buried in a proptosed supra-pubic mound.

When done in conjunction with a phalloplasty the graft donation site can be the supra-pubic area and the size of the incision is largely determined by the size of the graft required to widen the penis by the technique of dermal fat grafting described above.

The incision (previously determined by the size of required grafts for widening) is an elliptical incision widest in the midline and narrowest laterally both right and left and is made in the supra-pubic area and a block of skin and fat is removed down to the level of the external oblique. Dermal fat grafts are harvested from this excised skin/fat block which is divided in the midline vertically so as to produce two grafts of equal size.

The grafts are harvested by making an initial incision in the skin and then by sharp dissection removing the epidermis. The resultant dermis and fat block is then excised enmasse divided in two and used as the two grafts. The infra-pubic space is then developed in the same way as for penile lengthening.

When the deep stay sutures are in place two×0 maxon sutures are used to approximate the gracilus in front of the displaced penis and one×1 nylon deep stay suture is placed in the front of the pubic symphysis and this will be used to bring the skin just proximal to the base of the penis down onto the front of the pubic symphysis.

At this stage, the penis is de-gloved and the grafts sutured in place as for penile widening with dermal fat grafts.

After the grafts are in place and the penile skin has been reduced the nylon stay suture is inserted as described and this midline skin proximal to the penis is fixed to the front of the pubic symphysis on its infra-pubic surface. The tissues on either side are then elevated and sutured to the external oblique upon-neurosis using 1 nylon interrupted sutures.

Closure of the superior border of the defect created by extracting the grafts is achieved with a combination of undercutting of the fat against the external oblique upon-neurosis combined with a vertical plication of the external oblique sufficient to allow approximation of the two edges of skin without tension.

Deep stay suture on the front of the symphysis pubis and the attachment of the inferior margin of the wound to the external oblique and the longitudinal plication of the external oblique in order to bring the upper margin down so that closure is achieved without tension and the whole effect being to raise the infra-pubic and para-penile tissues back up onto the upper surface of the pubic bone and lower abdominal wall.

Enhancement with Artificial Erection Device

In its broadest aspect, the invention includes a method of enhancement phalloplasty of a human penis including the steps of degloving the penis to expose Buck's fascia and dividing the corpora cavernosa circumferentially after freeing the dorsal neurovascular bundles and separating the corpus spongiosum from the inferior surface of both corpora cavernosa.

The method can provide an increase in length of the penis of the order of one centimeter and thus the corporal cylinder to be used is longer by this amount than that presently in place or that which was measured when the corporotomy and dilatation of the corpus was performed earlier in the procedure.

The particular application to which the procedure specifically relates is to penile lengthening in patients who are about to have or already have in place an artificial erection device either of the inflatable or solid rod type as treatment for their impotence and who require additional penile lengthening and/or widening.

In association with the method of the invention, I can also apply the lengthening and widening techniques described earlier in this specification in conjunction with the treatment regimes earlier described.

The dissection involves separating the corpus spongiosum from the inferior surface of both corpora cavernosa. Additional length of 1 cm or more in the length of the corpus cavernosum can be obtained by this technique and so it will be necessary to either put a 1 cm longer corporal cylinder than has already been in place or a 1 cm longer cylinder than has been measured at the earlier part of the procedure when the corporotomy and dilatation of the corpus was performed. The gap in the corpus cavernosum is filled by suturing in place an inverted dermal graft from which the epidermis has been removed so that the dermo epidermal surface is the inner most surface applied to the corporal cavity.

Suturing is achieved using a continuous non-absorbable suture of the gortex type and suturing is performed over the deflated corporal cylinder (in the case of inflatable cylinders) or over the rigid non-inflatable intra corporal rod if this has been used.

If widening using a dermal fat graft is also desired then the dermal fat graft is sutured in place generally as described in my earlier patent application but when the graft reaches the defect in Buck's fascia corresponding to the division of the corpus cavernosum the edges of the graft are sutured to this circumferentially and to the distal portion of the corpus cavernosum without dividing the graft as a separate phenomenon. However in those patients in whom there is a very thickened wall of the corpus cavernosum a better result can be achieved by putting a separate dermal graft into the defect and then applying another dermal fat graft more superficially to that as described earlier in this specification. The same result can be achieved by filling the gap in the wall of the corpus cavernosum by using a gortex graft, a saphenous or other vein patch, temporalis or other fascia such as the fascia lata. Even substances such as dexon mesh or silastic sheeting are also theoretically possible.

In order that the invention may be more readily understood, I will describe one particular operation in which the use of the invention is demonstrated.

This operation may be combined with penile lengthening or lengthening and widening as described earlier in this specification or it may be performed alone. It should also be noted that the artificial erection device can be put in by the classic infrapubic or penoscrotal technique. If the latter is used it will be necessary to perform the penile lengthening by dividing the suspensory ligament having approached it by a vertical (or other) suprapubic incision.

Once the suspensory ligament of the penis and the deep stay sutures have been inserted as described above then the artificial erection device is inserted as per the classical description of the operation via the infrapubic or penoscrotal route as described widely in the general urological and surgical literature. Since additional length in the corpora cavernosa will be achieved by the technique of corporal division which is described hereinafter, the length of the corporal cylinder chosen for the artificial erection device should be 1 cm or longer than that already measured for the insertion of that device. If the device has previously been inserted at a previous operation then it will be necessary to reopen the corporal cylinder and either attach a further 1 cm rear tip extender or put in the same number of rear tip extenders as put in at the previous operation and add a 1 cm longer cylinder which must be new or some combination of those two possible techniques.

Once the artificial erection device is in place the penis is degloved, the artificial erection device fully inflated and the dorsal neurovascular bundle of the penis on either side of the midline dissected free from an area approximately 2 cm proximal to the coronal groove. This dissection is carried proximally and distally for 1 cm so that the entire area of mobilisation is at least 2 cm long. At the midpoint of this dissection the underlying corpus cavernosum on either side is incised and that incision is carried around medially in the midline or laterally around to the junction with the corpus spongiosum. This latter structure is then carefully dissected away from the corpus cavernosum so that it is separated intact over an area of approximately 1 cm. The division of the corpus cavernosum is then completed. The artificial erection device is then fully inflated and maximum separation of the corpus cavernosa is achieved. At this stage a dermal graft taken from the original site of dermal fat graft donor area is stripped of its fat and sutured in the circumferential manner to the free margins of the corpus cavonosum using a continuous non-absorbable suture such as 20 Gortex. When the wall of the corpus cavernosum is quite thin and when widening of the shaft of the penis is also being simultaneously achieved using a dermal fat graft a separate dermal graft to fill this defect is not necessary and the deep layers of the dermal fat graft can be sutured to the free edges of the corpus cavonosum instead. During the suturing process it is both important more convenient for the artificial erection device to be deflated thereby minimising the risk of perforation of that device with the needle during the suturing process.

At this stage the degloved penis is then reduced, the distal penile skin incision is closed with a running absorbable suture, the deep stay sutures in the infrapubic region are tied, the proximal wounds are trimmed and closed in layers and dressings are applied.

If the artificial erection device has been in place for some time it is then inflated and left inflated for 24 hours. Dressings are then applied. If the artificial erection device has been put in at the time of surgery as a new device then it is left deflated and a tight circumferential penile dressing applied.

Fenestration Technique

In a variation of the above described technique for enhancement in the context of the existence of an artificial erection device the penis can be dismembered utilising the following alternative technique to circumferential division and graft in one place:

The fenestration technique comprises separation of the three corpora along the entire length of the penile shaft external to the perineum.

The corpora cavernoso are then incised from 12 o'clock to 6 o'clock on the right hand side of each corpus; a distance of approximately 1 cm (or more or less) between each incision. Then the left hand side of each corpus is incised from 12 o'clock to 6 o'clock midway between two adjacent right hand incisions and this series of alternate incisions is carried the entire length of the penile shaft.

Whilst I have described herein specific embodiments of the concepts of the present invention it is to be understood that variations can be made in this within the ambit of the invention.

For example a modification on the above fenestration technique can comprise lateral fenestration only of the corpora cavernosa with or without separation of the three corpora.

The invention claimed is:

1. A method of lengthening the penis of a male which includes the steps of placing the suspensory ligament under tension in the inferior direction; dividing the suspensory ligament against the body of the symphysis pubis down to the inferior pubic arch and along the inferior surface of both the right and left conjoined inferior pubic rami; effecting suturing to retain the penis released from the suspensory ligament in an inferior position by coapting the proximal medial attachments of the right and left gracilus muscle together ventral the released penis, dividing the fundiform ligaments, drawing the skin of the junction site of the scrotum and the perineum mediosuperiorally so as to attach it to the symphysis pubis thereby pushing the skin adjacent thereto along the newly exposed shaft of the penis and suturing this to retain this position; said method further including the step of following a post operative treatment regime.

2. The method of claim 1 followed by the insertion of additional sutures through the anterior surface of the symphysis pubis; said sutures also placed through the margins of the pubic skin wound and tied in such a manner as to pull suprapubic skin down infrapubically.

3. The method of claim 2 wherein the number of said additional sutures inserted is 1 or more.

4. The method of claim 3 wherein the number of said additional sutures is determined by the width of the symphysis pubis.

5. The method of claim 1 including the step of dividing the fundiform ligament prior to said step of drawing the skin of the junction site of the scrotum.

* * * * *

UNITED STATES PATENT AND TRADEMARK OFFICE
CERTIFICATE OF CORRECTION

| | | |
|---|---|---|
| PATENT NO. | : 7,273,449 B2 | Page 1 of 2 |
| APPLICATION NO. | : 10/520959 | |
| DATED | : September 25, 2007 | |
| INVENTOR(S) | : Colin Campbell Marshall Moore | |

It is certified that error appears in the above-identified patent and that said Letters Patent is hereby corrected as shown below:

Title Page Column 2 item 57 (Abstract), Line 2 - After "arch" delete "," and insert -- ; --, therefore.

Column 1, Line 66 - Delete "gracilus" and insert -- gracilis --, therefor.

Column 4, Line 29 - Delete "inerted" and insert -- inserted --, therefor.

Column 4, Line 31 - Delete "Maxom" and insert -- Maxon --, therefor.

Column 4, Line 63(approx.) - After "Dermal" insert -- Fat --, therefore.

Column 5, Line 3 - After "order of" delete "b".

Column 6, Line 29(approx.) - Before "five" delete "(".

Column 6, Line 30 - Delete "leg ," and insert -- leg, --, therefor.

Column 7, Line 48 - Delete "gracilus" and insert -- gracilis --, therefor.

Column 9, Line 47-48 - Delete "cavonosum" and insert -- cavernosum --, therefor.

Column 9, Line 54 - Delete "cavonosum" and insert -- cavernosum --, therefor.

Column 10, Line 19-22 - Delete "Then the left hand ……………..the entire length of the penile shaft." and insert the same on Col. 10, Line 20, below "incision." as a new paragraph, therefor.

UNITED STATES PATENT AND TRADEMARK OFFICE
CERTIFICATE OF CORRECTION

PATENT NO. : 7,273,449 B2
APPLICATION NO. : 10/520959
DATED : September 25, 2007
INVENTOR(S) : Colin Campbell Marshall Moore It is certified that error appears in the above-identified patent and that said Letters Patent is hereby corrected as shown below:

Column 10, Line 41(approx.) - In Claim 1, delete "gracilus" and insert -- gracilis --, therefor.

Signed and Sealed this

Fifteenth Day of April, 2008

JON W. DUDAS
*Director of the United States Patent and Trademark Office*